United States Patent [19]

Bredehorst et al.

[11] Patent Number: 4,764,462
[45] Date of Patent: Aug. 16, 1988

[54] DETECTABLY LABELED CEPHALOSPORIN ASSAY FOR BETA-LACTAMASE

[75] Inventors: Reinhard Bredehorst, Washington, D.C.; Abdolhossen Talebian, Arlington, Va.; Charles F. Hammer; Carl-Wilhelm Vogel, both of Washington, D.C.

[73] Assignee: Georgetown University, Washington, D.C.

[21] Appl. No.: 768,832

[22] Filed: Aug. 23, 1985

[51] Int. Cl.$^4$ .................. C12Q 1/34; C12Q 1/02; C12Q 1/04; C12Q 1/06; C12Q 1/10; C12N 9/96

[52] U.S. Cl. ........................ 435/18; 435/29; 435/34; 435/38; 435/39; 435/188; 435/810

[58] Field of Search ................. 435/18, 805, 810, 29, 435/34, 38, 39, 188; 436/529, 530, 531, 526, 527, 535

[56] References Cited

U.S. PATENT DOCUMENTS

| | | | |
|---|---|---|---|
| 3,830,700 | 8/1974 | O'Callaghan et al. | 435/34 |
| 4,448,880 | 5/1984 | Schindler et al. | 435/18 |
| 4,535,156 | 8/1985 | Blumbach et al. | 540/226 |

OTHER PUBLICATIONS

Sassiver, M. L. et al., "Structure–Activity Relationships Among the Semisynthetic Antibiotics," (Perlman, D. ed.), N.Y., Academic Press, 1977, pp. 87–160.
Decristoforo, G. et al., "Rapid Determination of Cephalosporins with an Immobilized Enzyme Reactor . . . ", Analytica Chimica Acta, 163 (1984), 73–84.
Sykes et al., Antimic. Agents and Chemother., 1, pp. 94–99 (1972).
O'Callaghan et al., Antimic. Agents and Chemoother., 1, pp. 283–288 (1972).
O'Callaghan et al., J. of Bacteriol., 110, pp. 988–991 (1972).
Ross et al., Methods for the Study of Antibiotics, Methods of Enzymology, 43, pp. 69–85 (1975).
Lucas, J. of Clinical Pathology, 32, pp. 1061–1065 (1979).
Yolken et al., J. of Pediatrics, 97, pp. 715–720 (1980).
Jones et al., J. of Clin. Microbiol., 15, pp. 677–683 (1982).
Yolken et al., J. of Immunol. Meth., 73, pp. 109–123 (1984).

Primary Examiner—Esther M. Kepplinger
Attorney, Agent, or Firm—Saidman, Sterne, Kessler & Goldstein

[57] ABSTRACT

This invention provides for a cephalosporin immobilized on a solid phase support comprising a beta-lactamase releasable, detectably labeled substituent at the 3-position thereof.

This invention also provides for an assay for detecting the presence of beta-lactamase enzyme in a sample comprising:

(a) immobilizing a cephalosporin on a solid phase support wherein at the 3-position of said cephalosporin is a detectably labeled substituent releasable by beta-lactamase;

(b) contacting said sample with the immobilized cephalosporin of step (a); and, (c) detecting the released substituent.

26 Claims, 1 Drawing Sheet

DETECTABLY LABELED CEPHALOSPORIN ASSAY FOR BETA-LACTAMASE

The present invention was made using funds of the United States Government. The Government has certain rights in this invention.

FIELD OF THE INVENTION

The present invention relates to a detectably labeled cephalosporin immobilized on a solid phase support for the detection of beta-lactamase.

BACKGROUND OF THE INVENTION

Beta-lactamases are enzymes which are synthesized by a large number of bacterial species, but not by mammalian tissues. The detection of beta-lactamase in a mammalian body fluid is often indicative of a bacterial infection. Although the beta-lactamases synthesized by different bacteria vary in their structure and in certain properties, all are capable of hydrolyzing the carbon-nitrogen bond of the beta-lactam ring of a penicillin or a cephalosporin. Thus, penicillin and cephalosporins have been studied and utilized as a means for detecting the presence of beta-lactamase enzymes. Ross et al., "Beta-Lactamase Assays," *Methods for the Study of Antibiotics* (1975), pages 69–85; Lucas, T. J., "An Evaluation of 12 Methods for the Demonstration of Penicillinase," *J. of Clinical Pathology* (1979), pages 1061–1065.

Previous means for detection of beta-lactamases have typically used colorimetric tests, such as iodometric assay to measure the amount of iodine needed to oxidize the product of the enzyme. Sykes et al., "Microiodometric Determination of Beta-Lactamase Activity," *Antimicrob. Agents and Chemotherapy*, February 1972, pp. 94–99. Other diagnostic tests used particular cephalosporin compounds which undergo a distinctive color change when hydrolyzed by beta-lactamases. O'Callaghan et al., "Novel Method for Detection of Beta-Lactamase by Using a Chromogenic Cephalosporin Substrate," *Antimicrob. Agents and Chemotherapy* (April 1972), pp. 283–288; Jones, "In Vitro Evaluation of Pyridine-2-Argo-p-Dimethylaniline Cephalosporin, A New Diagnostic Chromogenic Reagent, and Comparison with Nitrocefin, Cephacetrile, and Other Beta-Lactam Compounds," *J. of Clinical Microbiology*, April 1982, pp. 677–683; Ross et al., supra; and T. J. Lucas, supra. Carbon 14-labeled benzyl-penicillin has been used to detect the presence of beta-lactamases. Yolken et al., "Rapid Diagnosis of Infections Caused by Beta-Lactamase-Producing Bacteria by Means of an Enzyme Radioisotopic Assay," *J. of Pediatrics* (November 1980), pages 715–720. In this assay, $C^{14}$-penicillin and the sample were mixed together, then an aliquot transferred to a column packed with DEAE-Sephacel equilibrated with tris buffer. The beta-lactamase converted the penicillin to penicillinoic acid, resulting in a new carboxyl group with an increased affinity to a positively charged gel such as DEAE-Sephacel. The unreacted penicillinase was washed from the column, and the penicillinoic acid subsequently recovered and measured.

Recently, beta-lactamases have been used in enzyme immunoassays. Yolken et al., "The Use of Beta-Lactamase in Enzyme Immunoassays for Detection of Microbial Antigens," *J. of Immunological Methods* (1984), pp. 109–123.

A cephalosporin is any of a family of antibiotics related to penicillin. The cephalosporin molecule contains a fused beta-lactam-dihydrothiazine ring system, typically with an N-acyl side chain at the 7-position and a group attached to the dihydrothiazine ring at the 3-position. Substituents of cephalosporins than can accept an electron in the 3-position, readily leave the compound upon the hydrolysis of the beta-lactam ring. Thus, whenever a cephalosporin is hydrolyzed by a beta-lactamase, there is a concomitant qualitative release of the electron-accepting substituent at the 3-position. O'Callaghan et al., "Correlation between Hydrolysis of the Beta-Lactam Bond of the Cephalosporin Nucleus and Expulsion of the 3-Substituent," *J. of Bacteriology* (June 1972), pp. 988–991.

None of the aforementioned methods or assays for detecting the presence of beta-lactamases use a cephalosporin immobilized on a solid phase support comprising a beta-lactamase releasable, detectably labeled, substituent at the 3-position thereof.

SUMMARY OF THE INVENTION

This invention provides for a cephalosporin immobilized on a solid phase support comprising a beta-lactamase releasable, detectably labeled substituent at the 3-position thereof.

This invention also provides for an assay for detecting the presence of beta-lactamase enzyme in a sample comprising:

(a) immobilizing a cephalosporin on a solid phase support wherein at the 3-position of said cephalosporin is a detectably labeled substituent, releasable by beta-lactamase;

(b) contacting said sample with the immobilized cephalosporin of step (a); and (c) detecting the released substituent.

DETAILED DESCRIPTION OF THE PREFERRED EMBODIMENTS

Figure 1:
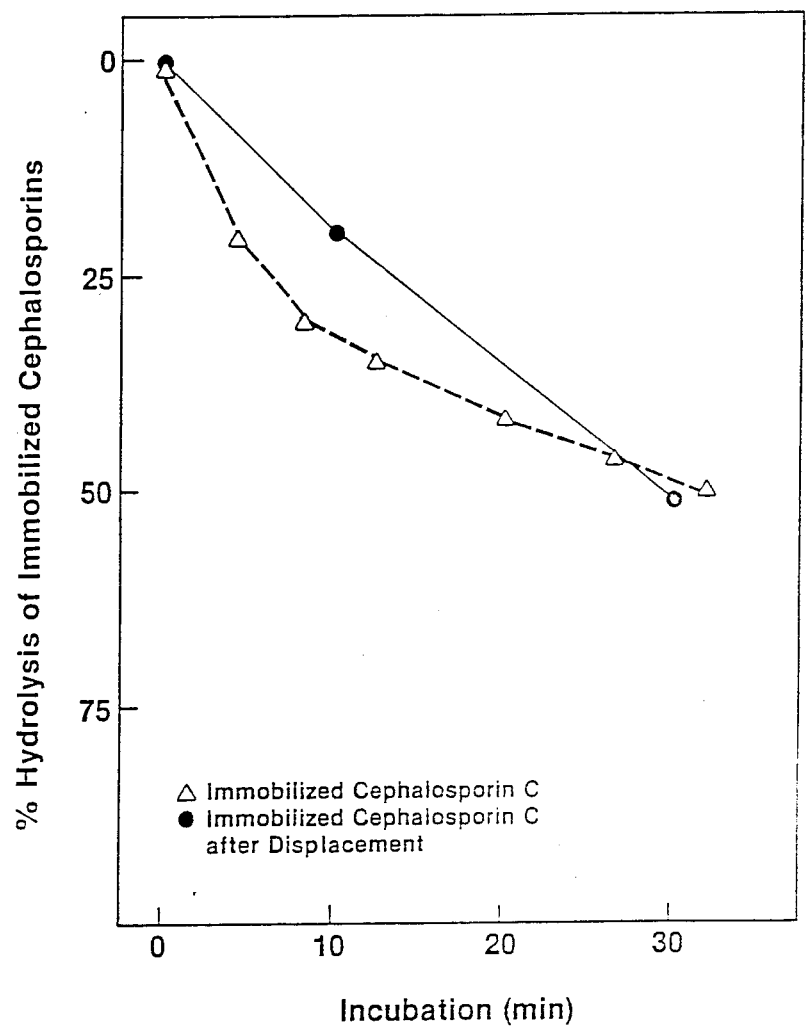
FIG. 1 shows the beta-lactamase enzymatic hydrolysis of immobilized cephalosporin C before and after displacement with N-(2-hydroxyethyl)-nicotinamide at the 3-position thereof.

In the practice of this invention, a cephalosporin with a releasable group at the 3-position is immobilized on a solid phase support system. The group at the 3-position is characterized by having a detectably labeled substituent. A sample containing the beta-lactamase enzyme contacts the immobilized, detectably labeled cephalosporin for a time and in such a manner that the detectably labeled substituent at the 3-position is released from the cephalosporin. The labelel substituent is then separated from the solid phase system, and detected according to means known in the art.

In one process embodiment of this invention, the cephalosporin is immobilized on the solid phase support, then the detectably labeled substituent is introduced at the 3-position of the cephalosporin.

In another process embodiment of this invention, the detectably labeled substituent is introduced to the 3-position of the cephalosporin prior to immobilizing the compound on the solid phase system.

Also in the practice of this invention, there is provided a novel substituent which can be used as the group introduced at the 3-position of the cephalosporin.

In the practice of this invention, any of the known cephalosporin compounds may be used, provided the group at the 3-position of the dihydrothiazine ring is able to accept electrons. Examples of such cephalosporins include, but are not limited to, cephacetrile, cephalexin, cephaloglycin, cephaloridine, cephalosporin C, cephalothin, cephamycins, cephapirin, cepharadine, and analogues and derivatives thereof, which are considered for purpose of the present invention to be equivalents. In the practice of the present invention, salts of cephalosporin compounds may also be used, such as alkali and alkaline earth metals, including sodium, potassium, magnesium, and calcium compounds, particularly cephacetrile sodium and cephapirin sodium; and other metal salts, such as iron, copper, nickel, and zinc compounds.

Examples of substituents at the 3-position may include any that are leaving groups, e.g. a substituent that can accept electrons, such that upon hydrolysis of the cephalosporin by a beta-lactamase, the substituent is released from its 3-position. As used herein, the 3-position of the cephalosporin is found by numbering the "S" on the dihydrothiazine ring as "1" and proceeding in a clockwise count. Weak bases comprise good leaving groups, and can be used as substituents, such as alkenes, alkoxide compounds, amines, ammonium, benzene compounds, carbonions, carboxylate compounds, piperidines, pyridines, pyrroles, quinolines, and thio compounds. The substituents at the 3-position according to the practice of this invention are also detectably labeled. This detectable labeling can include chromogenic, radioactive isotopes, fluorescent, chemiluminescent, or bioluminescent labels.

Those of ordinary skill in the art will know of other suitable labels for the 3position substituent, or will be able to ascertain such, using routine experimentation. Furthermore, the synthesis and displacement or binding of these labels to the cephalosporin can be done using standard techniques common to those of ordinary skill in the art. A number of reactions are known in the art which can be used to introduce the labeled substituent into the 3-position of the cephalosporin, including condensation, esterification, and cross-linking groups. (See March, J., *Advanced Organic Chemistry: Reactions, Mechanisms, and Structure* (McGraw-Hill 1968), pages 488–520, on aromatic nucelophilic substituents.)

The 3-position substituent can be detectably labeled using chromogenic moeities which can be detected, for example, by spectrophotometric means. Examples of chromogenic labels include azo compounds, specifically, pyridine-2-azo-p-dimethylanaline.

The 3-position substituent can also be detectably labeled with a radioactive isotope. The presence of the radioactive isotope can then be determined by such means as use of a gamma counter or a scintillation counter. Isotopes which are particularly useful are $^3$H, $^{125}$I, $^{131}$I, $^{32}$P, $^{35}$S, $^{14}$C, $^{51}$Cr, $^{36}$Cl, $^{57}$Co, $^{58}$Co, $^{59}$Fe, and $^{75}$Se.

It is also possible to detect the presence of the beta-lactamase by labeling the 3-position substituent with a fluorescent compound. When the fluorescent labeled substituent is exposed to light of the proper wavelength, its presence can then be detected due to fluorescence of the dye. Among the most important fluorescent labeling compounds are dansyl hydrazine, fluorescein isothiocyanate, rhodamine, phycoerythrin, phycocyanin, allophycocyanin, o-phthaldehyde, and fluorescamine.

Another way in which the 3-position substituent can be detectably labeled is by coupling it to a chemiluminescent compound. The presence of the chemiluminescent-tagged substituent is then determined by detecting the presence of luminescence that arises during the course of a chemical reaction. Examples of particularly useful chemiluminescent labeling compounds are luminol, isoluminol, aromatic acridinium ester, imidazole, acridinium salt, and oxalate ester.

Likewise, a bioluminescent compound may also be used to label the 3-position substituent. Bioluminescence is a special type of chemiluminescence which is found in biological systems and in which a catalytic protein increases the efficiency of the chemiluminescent reaction. The presence of a bioluminescent would be determined by detecting the presence of luminescence. Important bioluminescent compounds for purposes of labeling are luciferin, luciferase, and aequorin.

The cephalosporin according to the practice of the invention is immobilized on a solid phase support, preferably by immobilization of the cephalosporin at the 7-position thereof to the solid support. Any solid support system can be utilized, provided the group at the 7-position of the cephalosporin can attach and be immobilized.

Particularly preferred are solid phase systems wherein the cephalosporin is covalently coupled to an insoluble support so that the immobilized cephalosporin after contact with the beta-lactamase sample can be readily separated. A wide variety of solid phase supports have been described, which include particles of dextran, cellulose, continuous surfaces such as polystyrene or polypropylene discs, walls of plastic tubes, glass discs, glass particles, and the like. Particulate solid phases are widely used for a variety of different assays and are included in the present invention. Cephalosporins are attached to the particles by any of a number of techniques designed to yield a non-reversible covalent or non-covalent link between the cephalosporin and particle. Other alternatives are the use of cephalosporin entrapped in the interstices of a polyacrylamide gel, or bound to magnetic particles.

The assay tube is set up with a sample or a standard of beta-lactamase enzyme solution and the appropriate amount of solid phase immobilized detectably labeled cephalosporin. The sample or standard and immobilized cephalosporin are contacted for a sufficient period of time for the beta-lactamase to hydrolyze the cephalosporin, with the concomitant release of the detectably labeled substituent at the 3-position. As used herein, release is meant to include any cleavage or breaking of the bond attaching the 3-position substituent upon the hydrolysis of the beta-lactam ring by the action of a beta-lactamase enzyme.

The solid phase is then sedimented by centrifugation; the supernatant is removed; and the solid phase subject to washes with water or buffer in order to remove the released labeled substituent trapped within and between the particles. The labeled substituents in the supernatant are then measured. The remaining detectably labeled substituent still bound to the immobilized cephalosporin can also be measured.

The preferred method of preparing the immobilized cephalosporin is to first attach the cephalosporin to the solid phase support. By immobilizing the cephalosporin before displacement of the group at the 3-position with the labeled substituent, all unattached cephalosporin can be removed from the solid support (e.g., by washing or rinsing the support). The displacement of the group at the 3-position with the labeled substituent can then be done. All unattached labeled substituents can then be removed from the solid support following displacement. The advantages to this sequence of steps is that the system is easily purified by washing away the unbound cephalosporin and unattached labeled substituents. Alternatively, if the substituent is introduced into the 3-position of the cephalosporin prior to immobilization, then the detectably labeled cephalosporin must be separated from the unlabeled cephalosporin and evaluations conducted to ensure the purity of the labeled cephalosporin.

Samples containing beta-lactamase may include body fluids and the synthesis products from a bacteria culture. Different types of body fluids may include cerebrospinal fluid, pleural fluid, peritoneal fluid, urine, and blood. Since both pathogenic and non-pathogenic bacteria can produce beta-lactamase, the measurement of beta-lactamase in body fluids which are not normally sterile would not provide useful information. One of the advantages of this invention is that it is not affected by the presence of therapeutic levels of cephalosporins in the sample since only the detectably labeled substituents, either released or unreleased, are measured.

Gram-negative bacteria are the primary synthesizers of beta-lactamase, although gram-positive bacterial species also produce the enzyme. Although the beta-lactamases elaborated by different groups of bacteria vary in their structure, kinetic properties and substrate specificity, all are capable of hydrolyzing the beta-lactam ring of cephalosporins. Beta-lactamase producing bacteria include, but are not limited to, *S. aureus, S. epidermidis, E. coli, Enterobacter cloacae, P. morganii, Pseudomonas aeruginosa, H. influenza, N. gonorrhoeae, Bacillus cereus, Klebsiella pneumoniae, Serratia marcescens.*

In the preferred embodiment of this invention, the cephalosporin C compound is immobilized onto a solid phase support and the acetoxy group at the 3-position is displayed by a radioisotopic label, such as radioactive labeled N-(2-hydroxyethyl)nicotinamide.

Cephalosporin C is represented by the following formula (I):

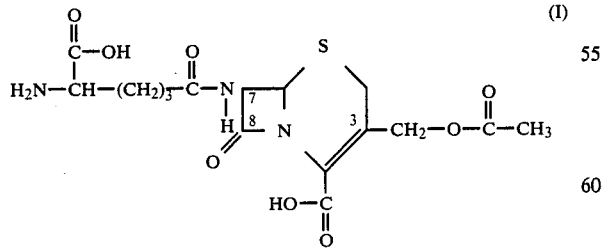

Immobilization of the cephalosporin C was achieved by the coupling of its terminal amino group of the 7-position chain to carbonyldiimidazole-activated glycerol-coated controlled pore glass beads, as shown in formula (II), by mixing the beads and the compound in a borate buffer solution (pH 8.1). Any non-immobilized cephalosporin C was washed from the support.

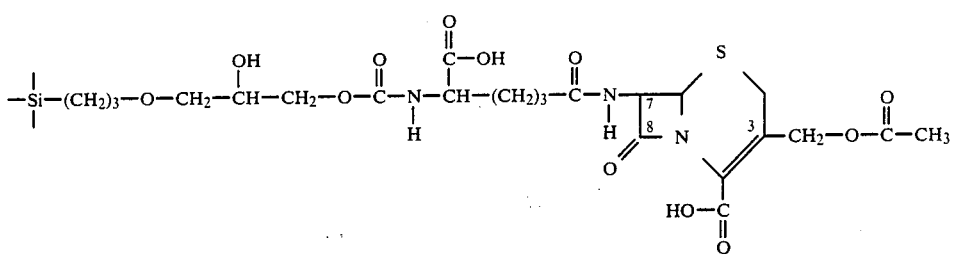

The acetoxy group at the 3-position of the cephalosporin C was displaced by N-(2-hydroxyethyl)-nicotinamide. The N-(2-hydroxyethyl)-nicotinamide was synthesized by a carbodiimide-mediated condensation of nicotinic acid (Formula III) and N-hydroxy-succinimide (Formula IV) in dimethylsulfoxide.

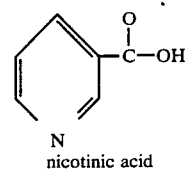

nicotinic acid

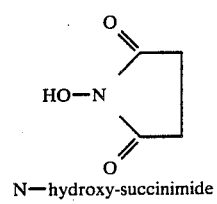

N—hydroxy-succinimide

The succinimidyl moiety of this compound, N-succinimidyl-nicotinate (Formula V) allows easy introduction of fluorescent or radioactive labels.

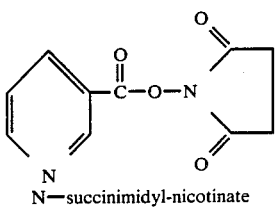

N—succinimidyl-nicotinate

For example, ethanolamine, available in radioactive form, was reacted with the N-succinimidyl-nicotinate to produce N-(2-hydroxyethyl)-nicotinamide (Formula VI).

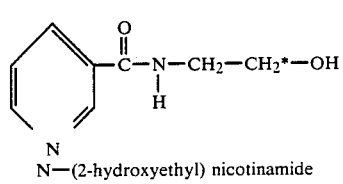

N—(2-hydroxyethyl) nicotinamide

The resulting radioactively labeled N-(2-hydroxyethyl)-nicotinamide was used to displace the acetoxy group at the 3-position of the immobilized cephalosporin C using the KSCN procedure described in Spencer et al., "Chemistry of Cephalosporin Antibiotics," *J. Org. Chem.* (1967), pp. 500–501.

The percentage hydrolysis of the immobilized cephalosporin was analyzed before and after displacement of the acetoxy group at the 3-position. Since the cephalosporin C was immobilized, it was not certain that the compound would still function as a substrate for the beta-lactamase enzyme reaction. However, the immobilized cephalosporin C does function as a substrate for beta-lactamase. FIG. 1 shows the enzymatic hydrolysis of the immobilized cephalosporin C before and after displacement with N-(2-hydroxyethyl)-nicotinamide.

The application of immobilized N-(2-hydroxyethyl)-nicotinamide cephalosporin is shown in the following formulae (VII) and (VIII), depicting the hydrolysis of the beta-lactam ring and the release of the 3-position substituent:

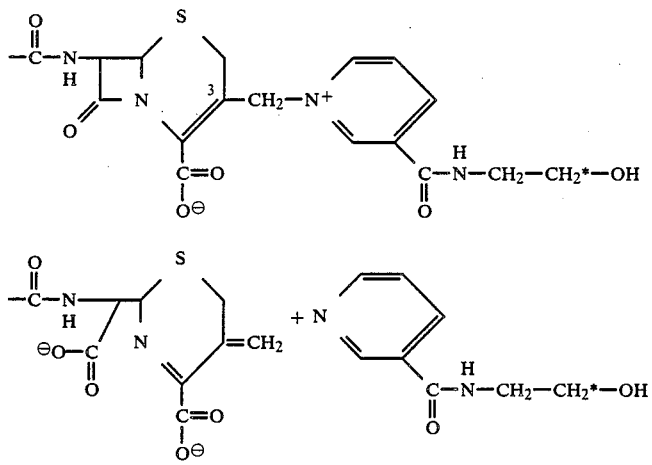

In the preferred embodiment, the detectably labeled substituent is a radioactive label. The radioactive label will be more sensitive to the presence of beta-lactamase, hence it will detect low levels of the enzyme. For samples comprising body fluids, the radioactive labels will be able to detect a beta-lactamase infection sooner, at a lower level of the enzyme present in the sample than with other labels.

The materials for use in the assay of the invention are ideally suited for the preparation of a kit. Such a kit may comprise a carrier means being compartmentalized to receive in close confinement one or more container means such as vials, tubes and the like, each of said container means comprising one of the separate elements to be used in the method.

For example, one of the said container means may comprise the immobilized, detectably labeled cephalosporin on the solid phase support. A second container may comprise a buffer for washing the immobilized cephalosporin. The carrier means may also contain a third container means for collecting the supernatant containing the released detectably labeled substituent.

In addition, the carrier means may also contain a plurality of containers each of which comprises different, predetermined amounts of known beta-lactamase. These latter containers can then be used to prepare a standard curve from which can be interpolated the results obtained from the sample containing the unknown amount of beta-lactamase.

In using the kit all a user has to do is add, to the container with the immobilized cephalosporin, a pre-measured amount of a sample containing the measurable, yet unknown amount of beta-lactamase. After an appropriate time for reaction, the cephalosporin is hydrolyzed and the detectably labeled substituent at the 3-position released. The container is washed with the buffer in the second container and the supernatant fluid is separated into the third container. The supernatant fluid is detected, as by radioactive counting or color development.

EXAMPLE 1

Preparation of N-succinimidyl-nicotinate

Molar equivalents of nicotinic acid (5.34 grams) and N-hydroxysuccinimide (5 grams) were dissolved in a minimum amount of dimethylsulfoxide. Then a 1.05 molar equivalent of 1,3-dicyclohexylcarbodiimide (DCC) was added to the mixture in small portions under $N_2$ atmosphere. The reaction mixture was slurried at room temperature until thin-layer chromatography (TLC) showed completion of the reaction. The DCC formed urea, which precipitated and was filtered out and the filtrate was washed with ethyl acetate (EtoAc). The solvent was removed under high vacuum, leaving an oily residue, which was then triturated with ether. The precipitate was filtered and recrystallized from ethyl acetate/petroleum ether. The product produced was N-succinimidyl-nicotinate, with a melting point 136°–137° C.; an $R_f$ value of 0.70 (TLC: silica; chloroform/methanol (10:1)); and a yield of 92%.

EXAMPLE 2

Synthesis of a Model Substituent for the 3-Position of Cephalosporins

Ethanolamine, $H_2N-CH_2CH_2-OH$, was used for the modification of the nicotinate derivative described in Example 1 to form N-(2-hydroxyethyl)-nicotinamide.

The ethanolamine was dissolved in dried N,N-dimethyl formamide (DMF) and chilled in an ice bath. The nicotinate derivative, also dissolved in DMF, was added to the DMF-amine mixture, dropwise under a nitrogen atmosphere. As the nicotinate derivative was added, the mixture turned milky and was slurried for at least one half hour. The milky substance was the N-hydroxy-succinamide precipitating, which was filtered off. The DMF-mixture was washed with ether to remove any precipitant. The solvent mixture was removed under high vaccum. The oily residue was triturated with ether, yielding a precipitant, N-(2-hydroxyethyl)-nicotinamide, which was recrystallized from ethyl acetate/petroleum ether. This compound had a melting point of 86°–87° C.; and $R_f$ value of 0.30 (TLC: silica: chloroform/methanol (10:1)); and a yield of 73%.

EXAMPLE 3

Synthesis of Radioactive Isotope Labeled Substituent for the 3-Position of Cephalosporins The N-succinimidyl-nicotinate compound described in Example 1 was reacted with the hydrochloric salt of ethanolamine, available commercially in its radioactive form. The ethanolamine salt was dissolved in dried DMF and chilled in an ice bath. To the mixture was added an equimolar of diisopropylethylamine (DIEA) and stirred for 15 minutes. An equimolar solution of N-succinimidyl-nicotinate was added to the ethylamine-DMF mixture dropwise under a nitrogen atmosphere. As the nicotinate was added the mixture turned milky and was slurried for at least another half hour. The milky substance was the N-hydroxy-succinimide precipitating, which was filtered off. The DMF-mixture was washed with ether to remove any precipitant. The solvent mixture was removed under high vaccum. The oily mixture was triturated with ether to yield a precipitant, N-(2-hydroxyethyl)nicotinamide. The radioactive compound was isolated and identified by its TLC.

EXAMPLE 4

Immobilization of Cephalosporin on Solid Phase Support

Cephalosporin C was added to 100 mg of carbonyl diimidazole-activated glycerol-coated controlled pore glass beads (90–150 μm diameter beads) in a 100 mM borate buffer at a pH of 8.1. The cephalosporin C in the borate buffer was mixed with the beads in end-over-end mixing overnight for two days at room temperature. The beads were then washed several times with water to remove any unbound cephalosporin C. The beads were then analyzed by iodometric assay and enzymatic beta-lactamase assay for the efficiency of the degree of immobilization of cephalosporin C.

Reagent:

Starch/Iodine Solution: Starch (Sigma S4501) was dissolved in 200 ml of 0.1M potassium phosphate buffer by boiling for 20 minutes to yield a 0.2% hydrolyzed starch solution. An iodine/potassium iodide solution in phosphate buffer (10 mM, 200 mM) was prepared. This solution was added to the starch/buffer solution in an 1:8 ratio, yielding a final starch/iodine solution. The starch/iodine solution had an absorption at 570 nm of approximately 1.0. The solution was stored at 4° C.

Iodometric method: 25 ul of 0.5M NaOH was added to a 100 ul aliquot containing a known concentration of immobilized cephalosporin C and mixed at 37° C. for 30 minutes. To this mixture was added 50 ul of 0.2M sodium buffer, 25 ul of 0.5M HCl, and 65 ul of starch/iodine, to a final volume of 265 ul. After a reaction time of 90 minutes, 200 ul of the mixture was read at 570 nm on a spectrophoto-meter. The results are as follows:

Blank = 1.196
Beads without NaOH: 1.013
Beads with NaOH: 0.677
Degree of the efficiency of immobilization: 0.677–1.196 = 56.6% (53 nmoles of cephalosporin C/50 mg of beads.)

EXAMPLE 5

Displacement of the 3-Position Acetoxy Group of the Cephalosporin C with the Labeled N-(2-hydroxyethyl)-nicotinamide Cephalosporin C immobilized on 350 mg of beads suspended in 0.5 ml of water, was incubated with 10 ul of N-(2-hydroxyethyl)-nicotinamide (the labeled substituent) dissolved in DMF (approximately 4M) and approximately 2 grams of KSCN (saturation). This mixture was end-over-end mixed in a water bath at 60° C. for 5 hours. The beads were then washed several times with water and suspended in 5 ml of water.

Successful displacement of the substituent at the 3-position was determined. Various concentrations of the immobilized and labeled cephalosporin C were treated with 25 ul of 0.5M NaOH at 37° C. for 30 minutes and treated with 25 ul of 0.5M HCl. The supernatant containing the released radioactive label was counted with a beta-counter. The results are shown in Table I.

TABLE I

| Sample Supernatant | Counts per minute (cpm) | Disintegration per minute (dpm) |
| --- | --- | --- |
| Blank-control | 19.0 | 38.1 |
| 0.2 mg | 30.0 | 76.7 |
| 1 mg | 94.0 | 324.7 |
| 5 mg | 397.0 | 1,480.6 |
| 10 mg | 616.0 | 2,348.8 |
| 20 mg | 971.0 | 3,793.6 |

EXAMPLE 6

Susceptibility of Immobilized Cephalosporin C to Enzymatic Hydrolysis

Cephalosporin was immobilized as described in Example 4. A portion of the immobilized cephalosporin C was displaced at the 3-position with N-(2-hydroxyethyl)-nicotinate as described in Example 5.

The susceptibility of the immobilized cephalosporin C before and after displacement to enzymatic degradation by beta-lactamase from *Ent. cloacae* was determined.

Reagents:

Borate buffer: 1 liter of buffer made by adding 0.1M boric acid and adjusting the pH to 8.1 with 5M NaOH. The buffer was stored at 4° C.

Starch/iodine solution: prepared as previously described in Example 4.

Procedure:

To borate buffered solutions of the immobilized cephalosporin C before and after displacement at the 3-position of known concentrations was added a borate buffered solution of beta-lactamase from *Ent. cloacae* of known concentration. At 4 minute time intervals of incubation at room temperature, 200 ul aliquots of the supernatants were removed, incubated with starch/iodine solution for 90 minutes, and subsequently the absorbance was determined at 570 nm as described in Example 4.

The blank consisted of borate buffer and starch/iodine solution.

The controls consisted of (a) borate buffer, starch/iodine solution and substrate and (b) borate buffer, starch/iodine solution and enzyme.

FIG. 1 shows the time course of the enzymatic degradation of the immobilized cephalosporin C before and after displacement.

Although the foregoing invention has been described in some detail be way of illustration and example for purposes of clarity and understanding, it will be obvious that certain changes and modifications may be practiced within the scope of the invention, as limited only by the scope of the appended claims.

We claim:

1. A cephalosporin immobilized on a solid phase support at the 7-position of said cephalosporin with a beta-lactamase releasable, detectably labeled substituent at the 3-position of said immobilized cephalosporin.

2. The cephalosporin of claim 1 wherein said cephalosporin is selected from the group consisting of cephacetrile, cephalexin, cephaloglycin, cephaloridine, cephalosporin C, cephalothin, cephamycins, cephapirin, and cephradine.

3. The cephalosporin of claim 2 wherein said cephalosporin is cephalosporin C.

4. The cephalosporin of claim 1 wherein said solid phase support is selected from the group consisting of dextran, cellulose, polystyrene, polypropylene discs, walls of plastic tubes, glass discs, glass particles, polyacrylamide gel, and magnetic particles.

5. The cephalosporin of claim 1 wherein said solid phase support is controlled pore glass beads.

6. The cephalosporin of claim 1 wherein said detectably labeled substituent is selected from the group consisting of chromogenic, radioactive isotopes, fluorescent, chemiluminescent, and bioluminescent labels.

7. The cephalosporin of claim 1 wherein said detectably labeled substituent is a chromogenic label.

8. The cephalosporin of claim 7 wherein said chromogenic label is selected from azo compounds.

9. The cephalosporin of claim 1 wherein said detectably labeled substituent is a radioactive isotope.

10. The cephalosporin of claim 9 wherein said radioactive isotope is selected from the group consisting of $^{3}H$, $^{125}I$, $^{32}P$, $^{35}S$, $^{14}C$, $^{51}Cr$, $^{36}Cl$, $^{57}Co$, $^{59}Fe$ and $^{75}Se$.

11. The cephalosporin of claim 1 wherein said detectably labeled substituent is a fluorescent label.

12. The cephalosporin of claim 11 wherein said fluorescent label is selected from the group consisting of dansyl hydrazine, fluorescein isothiocyanate, rhodamine, phyroerthrin, phycocyanin, allophycocyanin, o-phthaldehyde, and fluorescamine.

13. The cephalosporin of claim 1 wherein said detectably labeled substituent is a chemiluminescent label.

14. The cephalosporin of claim 13 wherein said chemiluminescent label is selected from the group consisting of luminol, isoluminol, aromatic acridinium ester, imidazole, acridinium salt, and oxalate ester.

15. The cephalosporin of claim 1 wherein said detectably labeled substituent is a bioluminescent label.

16. The cephalosporin of claim 15 wherein said bioluminescent label is selected from the group consisting of luciferin, luciferase, and aequorin.

17. The cephalosporin of claim 1 wherein said substituent is able to accept electrons.

18. The cephalosporin of claim 1 wherein said substituent is selected from the group consisting of alkenes, alkoxides, amines, benzenes, carbonions, piperidines, pyridines, pyrroles, quinolines and the thio compounds.

19. An assay for detecting the presence of beta-lactamase enzyme in a sample comprising:
 (a) immobilizing a cephalosporin at the 7-position thereof on a solid phase support wherein at the 3-position of said cephalosporin is a detectably labeled substituent releasable beta-lactamase;
 (b) contacting said sample with the cephalosporin of step (a); and
 (c) detecting the released substituent as a measure of the presence of beta-lactamase enzyme.

20. The assay of claim 19 wherein said sample is a body fluid selected from the group consisting of cerebrospinal fluid, pleural fluid, peritoneal fluid, urine, and blood.

21. The assay of claim 19 wherein said sample is the synthesis product of a bacterium.

22. A kit useful for the detection of a beta-lactamase enzyme in a sample comprising a carrier being compartmentalized to receive in close confinement therein one or more containers wherein
 (a) a first container contains a cephalosporin immobilized at the 7-position on a solid phase support and a beta-lactamase releasable, detectably labeled substituent at the 3-position of said cephalosporin; and
 (b) a second container contains a washing solution.

23. The kit of claim 22 wherein said first container contains cephalosporin selected from the group consisting of cephacetrile, cephalexin, cephaloglycin, cephaloridine, cephalosporin C, cephalothin, cephamycins, cephapirin, cephradine, and analogues, and salts thereof.

24. The kit of claim 22 wherein said cephalosporin is detectably labeled with a label selected from the group consisting of chromogenic, radioactive isotopes, fluorescent, chemiluminescent, and bioluminescent labels.

25. The kit of claim 22 wherein said solid phase support is selected from the group consisting of dextran, cellulose, polystyrene, polypropylene discs, walls of plastic tubes, glass discs, glass particles, polyacrylamide gel, and magnetic particles.

26. The kit of claim 22 further comprising a third container means for collecting the released, detectably labeled substituent.

* * * * *